United States Patent [19]

Abou-Gharbia

[11] Patent Number: 4,900,835

[45] Date of Patent: Feb. 13, 1990

[54] ANTIPSYCHOTIC IMIDES

[75] Inventor: Magid A. Abou-Gharbia, Glen Mills, Pa.

[73] Assignee: American Home Products Corporation, New York, N.Y.

[21] Appl. No.: 335,076

[22] Filed: Apr. 7, 1989

Related U.S. Application Data

[62] Division of Ser. No. 21,952, Mar. 5, 1987, Pat. No. 4,851,533.

[51] Int. Cl.$^4$ ............................................. C07D 401/06
[52] U.S. Cl. ................................... 546/272; 546/153; 546/157; 546/175
[58] Field of Search ................ 546/153, 157, 175, 272

[56] References Cited

PUBLICATIONS

Derwent Abstract 30495X/17 of DT 2544–382 (10/4/74).

*Primary Examiner*—Mary C. Lee
*Assistant Examiner*—J. Richter
*Attorney, Agent, or Firm*—Richard K. Jackson

[57] ABSTRACT

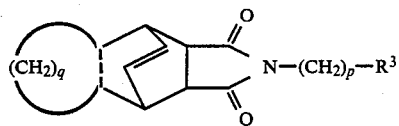

in which the dotted lines represent optional unsaturation;
p is one of the integers 2, 3, 4 or 5;
q is one of the integers 1, 2 or 3;
and

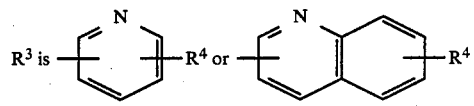

where
$R^4$ is hydrogen, alkyl, alkoxy or halo; or a pharmaceutically acceptable salt thereof are antipsychotic and anxiolytic agents.

3 Claims, No Drawings

ANTIPSYCHOTIC IMIDES

RELATED APPLICATIONS

This application is a division of U.S. Ser. No. 07/21,952, filed Mar. 5, 1987, now U.S. Pat. No. 4,851,533, by Magid A. Abou-Gharbia entitled "1,4-Diazine Derivatives".

DESCRIPTION OF THE INVENTION

In accordance with this invention there is provided a group of antipsychotic-anxiolytic agents of the formula:

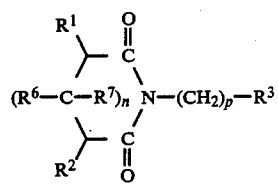

in which
n is one of the integers 0 or 1;
and
when n is 1, $R^1$ and $R^2$ are hydrogen or alkyl of 1 to 3 carbon atoms, and $R^6$ and $R^7$, taken together, are tetramethylene, pentamethylene or hexamethylene; and
when n is 0, $R^1$ and $R^2$, taken together, are

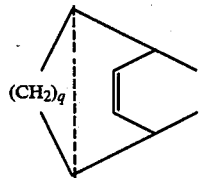

where
the dotted line represents optional unsaturation;
p is one of the integers 2, 3, 4 or 5;
q is one of the integers 1, 2 or 3;
and
$R^3$ is

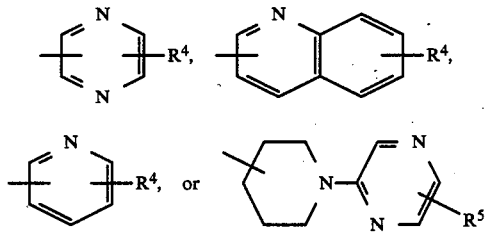

where
$R^4$ is hydrogen, alkyl of 1 to 6 carbon atoms; alkoxy of 1 to 6 carbon atoms or halo;
and
$R^5$ is hydrogen or halo; or a pharmaceutically acceptable salt thereof.

In the preceding description of the compounds of this invention, the term "halogen" is intended to embrace chlorine, bromine and fluorine and the pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds of this invention are readily prepared by a variety of conventional methods generally involving alkylation of the imide with $X-(CH_2)_p-R^3$ where X is chlorine or bromine, p is 2 to 5 and $R^3$ is the appropriately substituted pyridine or pyrazine moiety. Where $R^3$ is a substituted heterocyclic-piperidinyl moiety, the compounds are prepared by the alkylation described in the preceding sentence followed by reduction of the aromatic ring, as by hydrogenation (e.g. in $CH_3OH$ with 2% $Rh/Al_2O_3$ catalyst and glacial acetic acid) and N-alkylation in dimethylformamide with

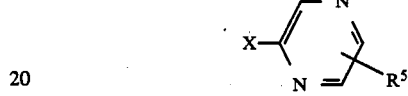

in the presence of cesium carbonate, where X is chlorine or bromine and $R^5$ is defined above. The reactants involved are either commercially available or are prepared by known procedures well within the skill of the chemist.

The antipsychotic properties of the compounds of this invention were established by the standard, pharmacologically accepted procedure involving a conditioned avoidance study in which trained male CD rats (Charles River), 400–450 g. body weight, are exposed to a fifteen second warning tone (conditioned stimulus) conditioned for an additional fifteen seconds accompanied by electric shock. The rat can avoid the electric shock by jumping to an exposed shelf (shelf-jump response). In this test situation, a response during the initial warning tone is considered an avoidance response while a response during shock delivery is considered an escape response. The avoidance response was determined and the compound being tested evaluated as active or inactive at the dose administered.

As a measure of extrapyramidal side effects, the compounds of this invention were studied as antagonists of apomorphine-induced stereotyped behavior wherein CF-1 mice (Charles River) receive the test compound i.p. (six mice per dose level) and thirty minutes later receive 10 mg./kg. apomorphine s.c. Five minutes after injection, the rearing-head-bobbing-licking syndrome induced by apomorphine is evaluated as present or absent for each animal. Readings are repeated every five minutes during a thirty minute test session. An $ED_{50}$ value (with 95% confidence intervals) is calculated for inhibition of apomorphine-induced stereotyped behavior by simple linear regression analysis. The compounds of this invention were inactive in this study. Thus, the compounds of this invention demonstrate a low potential for side effects which attends long term treatment with such standard antipsychotic drugs as haloperidol and chlorpromazine.

From these data, the activity profile of the compounds of this invention are seen to be that of antipsychotic agents with much lower potential for extra-pyramidal side effects such as attend the use of major tranquillizers (sedation, pseudoparkinsonism, ataxia, muscle relaxation, etc.). This activity profile resembles that of the anxiolytic compound buspirone.

Hence, the compounds of this invention are antipsychotic agents and anxiolytic agents useful in the treatment of psychoses such as paranoia and schizophrenia and in alleviating anxiety. As such, they may be administered neat or with a pharmaceutical carrier to a patient in need thereof. The pharmaceutical carrier may be solid or liquid.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intamuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of compounds of this invention. After each example the pharmacological evaluation for the compound produced is presented. The conditioned avoidance test is reported as self-jump (S-J) at the intraperitoneal (i.p.) dose administered in mg./kg. As indicated above, all the compounds of this invention were inactive as apomorphine antagonists.

EXAMPLE 1

4,4a,5,5a,6,6a-Hexahydro-2-[4-(4-pyridinyl)butyl]-4,6-ethenocycloprop[f]isoindole-1,3-(2H,3aH)-dione To a stirred solution of 2.2 g. (0.011 mol) of 1,3-dioxo-2H-4,6-etheno-1,3,3a,6a-tetrahydrocycloprop[f]isoindole in 50 ml. of dimethylformamide is added 3 g. (0.011 mol) of cesium carbonate and 3.2 g. (0.011 mol) of 4-pyridinylbutyl bromide hydrobromide. The reaction mixture is stirred at room temperature for 48 hours, dimethylformamide is evaporated under reduced pressure and the residue is extracted with methylene chloride ($3 \times 200$ ml.). The methylene chloride extracts are collected, washed with water, dried over anhydrous $Na_2SO_4$ and evaporated under reduced pressure. The semisolid residue was subjected to HPLC separated using ethyl acetate as eluent. Evaporation of the solvent from the desired fraction (TLC $R_f$ 0.13) affords 1.6 g. (45% yield) of the titled compound which is converted to the hydrochloride salt by dissolving the free base in ethanol and adding ethanol saturated with hydrogen chloride; m.p. 228°–230° C.

Analysis for: $C_{20}H_{22}N_2O_2 \cdot HCl$
Calculated: C, 66.94; H, 6.41; N, 7.81
Found: C, 66.61; H, 6.36; N, 7.82
S-J: Active (40 mg./kg.)

EXAMPLE 2

2-[4-[1-(6-chloro-2-pyrazinyl)-4-piperidinyl]butyl]-4,4a,5,5a,6,6a-hexahydro-4,6-ethenocycloprop[f]isoindole-1,3-(2H,3aH)-dione To an ethanolic solution of the compound of Example 1 (2 g.; 0.006 mol in 50 ml. of ethanol) under nitrogen was added 0.4 g. of rhodium over aluminium oxide and 1 ml. of glacial acetic acid.

The reaction mixture was hydrogenated at room temperature in a Barr shaker with hydrogen (50 psi) for 3 hours; then it was filtered and the solvent was removed under reduced pressure. The remaining oil was dissolved in 50 ml. of dimethylformamide and to that solution was added 0.5 g. of cesium carbonate and 1.1 g. (0.007 mol) of 2,6-dichloropyrazine. The reaction mixture was stirred at room temperature for 48 hours and following the same work up of Example 1, it afforded the title compound which was converted to the hydrochloride salt; m.p. 138°–140° C.

Analysis for: $C_{24}H_{29}ClN_4O_2 \cdot HCl$
Calculated: C, 60.37; H, 6.28; N, 11.74; Cl, 14.80
Found: C, 60.54; H, 6.64; N, 11.50; Cl, 14.18
S-J: Active (40 mg./kg.)

EXAMPLE 3

8-[4-(4-pyridinyl)butyl]-8-azaspiro[4.5]decane-7,9-dione

To a stirred solution of 1.8 g. (0.011 mol) of 3,3-tetramethyleneglutarimide in 50 ml. of dimethylformamide is added 3 g. (0.011 mol) of cesium carbonate and 3.2 g. (0.011 mol) of 4-pyridinylbutyl bromide hydrobromide. The reaction mixture is stirred at room temperature for 48 hours, dimethylformamide is evaporated under reduced pressure and the residue is extracted with methylene chloride (3×200 ml.). The methylene chloride extracts are collected, washed with water, dried over anhydrous $Na_2SO_4$ and evaporated under reduced pressure. The semisolid residue was subjected to HPLC separated using ethyl acetate as eluent. Evaporation of the solvent from the desired fraction (TLC $R_f$ 0.2) affords 1.0 g. (30% yield) of the titled compound which is converted to the hydrochloride salt by dissolving the free base in ethanol and adding ethanol saturated with hydrogen chloride; m.p. 155°–157° C.

Analysis for: $C_{18}H_{24}N_2O_2HCl\frac{1}{2}H_2O$
Calculated: C, 62.51; H, 7.52; N, 8.10
Found: C, 62.74; H, 7.22; N, 8.44
S-J: Active (40 mg./kg.)

EXAMPLE 4

4,5,6,7,8,8a-Hexahydro-2-[4-(4-pyridinyl)butyl]-4,8-ethenocyclohepta[c]pyrrole-1,3-(2H;3aH)dione To a stirred solution of 1.9 g. (0.01 mol) of hexahydro-4,8-ethenocyclohepta[c]pyrrole-1,3-(2H, 3aH)dione in 50 ml. of dimethylformamide is added 3 g. (0.01 mol) of cesium carbonate and 3.2 g. (0.01 mol) of 4-pyridinylbutylbromide hydrobromide.

The reaction mixture is stirred at room temperature overnight and dimethylformamide is evaporated under reduced pressure.

The remaining residue is extracted with 3×200 ml. of $CH_2Cl_2$, washed with water, dried and evaporated under reduced pressure.

The separated solid was converted to the hydrochloride salt; m.p. 190°–192° C.

Analysis for: $C_{20}H_{24}N_2O_2HCl\frac{1}{2}H_2O$
Calculated: C, 64.95; H, 7.03; N, 7.57
Found: C, 65.42; H, 7.01; N, 7.69
S-J: Active (40 mg./kg.)

What is claimed is:

1. A compound of the formula:

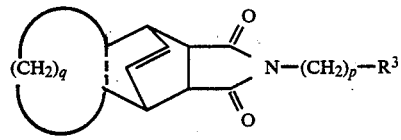

in which
the dotted lines represent optional unsaturation;
p is one of the integers 2, 3, 4 or 5;
q is one of the integers 1, 2 or 3;
and

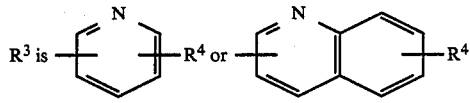

where
$R^4$ is hydrogen, alkyl of 1 to 6 carbon atoms; alkoxy of 1 to 6 carbon atoms or halo;
or a pharmaceutically acceptable salt thereof.

2. The compound of claim 1 which is 4,4a,5,5a,6,6a-hexahydro-2-(4-(4-pyridinyl)butyl)-4,6-ethenocycloprop(f)isoindole-1,3-(2H,3aH)-dione.

3. The compound of claim 1 which is 4,5,6,7,8,8a-hexahydro-1-(4-(4-pyridinyl)butyl)-4,8-etheno-cycloheptal(c)pyrrole-1,3-(2H)-dione.

* * * * *